US00PP26520P3

(12) United States Plant Patent
Danziger

(10) Patent No.: US PP26,520 P3
(45) Date of Patent: Mar. 15, 2016

(54) ***SALVIA* PLANT NAMED 'DSALRS203'**

(50) Latin Name: *Salvia sylvestris*
Varietal Denomination: DSALRS203

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 124 days.

(21) Appl. No.: 13/999,986

(22) Filed: Apr. 11, 2014

(65) Prior Publication Data

US 2015/0296680 P1 Oct. 15, 2015

(51) Int. Cl.
*A01H 5/00* (2006.01)

(52) U.S. Cl.
USPC ..... Plt./475

(58) Field of Classification Search
USPC ..... Plt./475
See application file for complete search history.

*Primary Examiner* — Annette Para
(74) *Attorney, Agent, or Firm* — Cassandra Bright

(57) ABSTRACT

A new and distinct *Salvia* cultivar named 'DSALRS203' is disclosed, characterized by early flowering, compact plant habit, large flowers and short flowering stems. The new variety is a *Salvia,* normally produced as an outdoor garden or container plant.

2 Drawing Sheets

Figure 1:
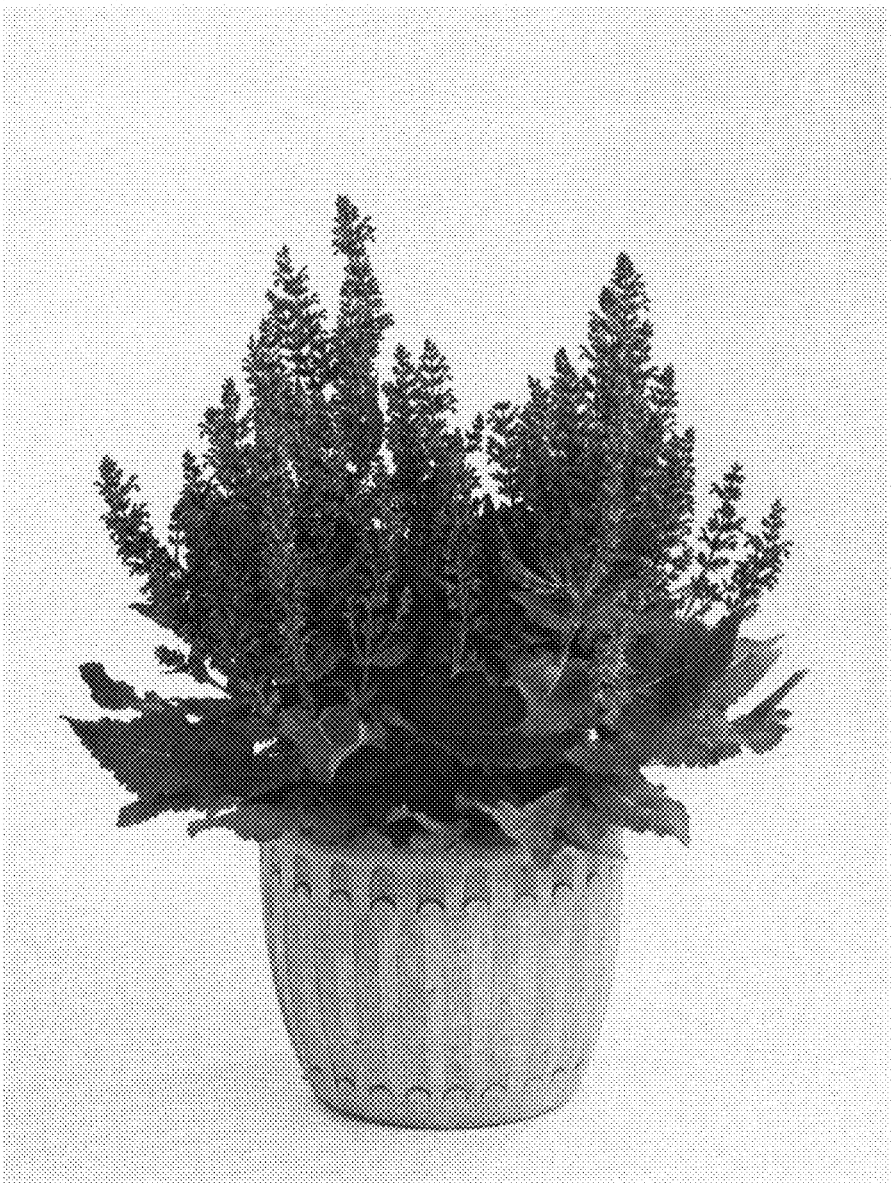

Latin name of the genus and species *Salvia sylvestris.*
Variety denomination: 'DSALRS203'.

BACKGROUND OF THE INVENTION

The new *Salvia* cultivar is a product of a planned breeding program conducted by the inventor, Gavriel Danziger, in Moshav Mishmar Hashiva, Israel. The objective of the breeding program was to produce new *Salvia* varieties for ornamental commercial applications. The open pollination resulting in this new variety was made during April of 2007.

The seed parent is the unpatented, proprietary seedling variety referred to as *Salvia sylvestris* 'SAN-Z-1' The pollen parent is unknown as it was an open pollination breeding program. The new variety was discovered in August of 2008 by the inventor in a group of seedlings resulting from the 2007 open pollination, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel during November of 2008 and has shown that the unique features of this cultivar are stable and reproduced true to type in about 70 successive generations.

SUMMARY OF THE INVENTION

The cultivar 'DSALRS203' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DSALRS203' These characteristics in combination distinguish 'DSALRS203' as a new and distinct *Salvia* cultivar:

1. Compact habit.
2. Large flowers

3. Short flowering stems.
4. Early flowering.

Plants of the new cultivar 'DSALRS203' are similar to plants of the seed parent, *Salvia sylvestris* 'SAN-Z-1' in most horticultural characteristics, however, plants of the new cultivar 'DSALRS203' differs in the following:

1. More compact plant.
2. Earlier flowering.
3. Shorter flowering stems.

COMMERCIAL COMPARISON

Plants of the new cultivar 'DSALRS203' are comparable to the unpatented commercial variety *Salvia* 'May Night'. The two *Salvia* varieties are similar in most horticultural characteristics; however, the new variety 'DSALRS203' differs in the following:

1. Comparison variety height is 30-45 cm, whereas candidate variety is 25-30 cm.
2. Comparison variety spread is 30-35 cm, whereas the candidate variety is 20-30 cm.
3. Candidate variety begins blooming earlier in the Spring, by approximately 1 month.

Plants of the new cultivar 'DSALRS203' are also comparable to the unpatented commercial variety *Salvia* 'Snowhill'. The two *Salvia* varieties are similar in most horticultural characteristics; however, the new variety 'DSALRS203' differs in the following ways:

1. Comparison variety has mounded growth habit whereas candidate variety has upright growth habit.
2. Comparison variety has white flowers whereas candidate variety has purple flowers.
3. Comparison variety spread is 30-40 cm, whereas the candidate variety is 20-30 cm.

BRIEF DESCRIPTION OF THE PHOTOGRAPHS

The accompanying photograph in FIG. 1 illustrates in full color a typical plant of 'DSALRS203' grown in a greenhouse, in a 13 cm pot. Age of the plant photographed is approximately 3 months old from rooted cutting.

Figure 2:
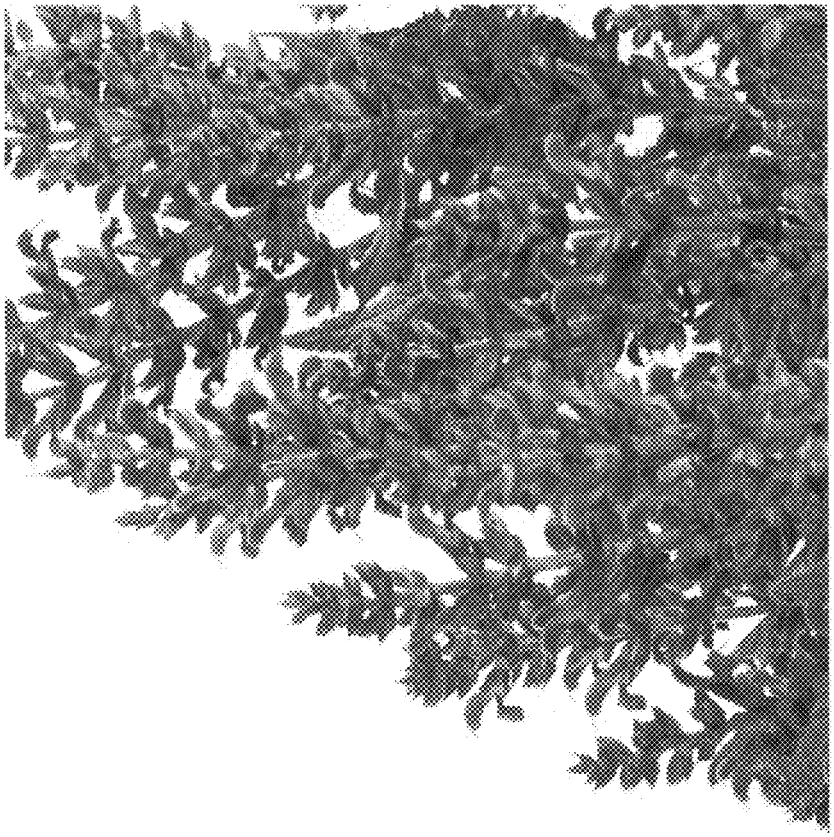

FIG. 2 illustrates a close up of the inflorescence.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DSALRS203' plants grown in a greenhouse during Winter to Spring in Moshav Mishmar Hashiva, Israel. The growing temperature ranged from 15° C. to 26° C. during the day and from 13° C. to 16° C. during the night. Measurements and numerical values represent averages of typical plant types.

Botanical classification: *Salvia sylvestris* 'DSALRS203'.

PROPAGATION

Time to initiate roots: About 5-7 days at approximately 18-24° C.

Time to produce a rooted cutting: About 10-14 days at 18-24° C.

PLANT

Age of plant described: Approximately 12 weeks from a rooted cutting.

Overall plant shape or growth habit: Upright.

Plant spread: Approximately 25-30 cm.

Plant height: Approximately 25-30 cm.

Growth rate: Moderate — fast.

Length of primary lateral branches: Approximately 6 cm.

Diameter of lateral branches: Approximately 0.4 cm

Quantity of lateral branches: About 15.

*Color.*—Near yellow-green 144A RHS.

*Texture/pubescence.*—Lightly pubescent with soft, short feathers like hairs. Slightly ribbed longwise.

Internode length: Approximately 1.5-2 cm.

FOLIAGE

Leaf:

*Arrangement.*—Alternate.

*Quantity.*—Approximately 10-20 per main branch.

*Average length.*—Approximately 6-8 cm.

*Average width.*—Approximately 2-3 cm.

*Shape of blade.*—Deltoid.

*Apex.*—Acute to nearly acuminate.

*Base.*—Cordate.

*Attachment.*—Petiolate.

*Margin.*—Crenate.

*Texture of top surface.*—Slightly coarse due to sunken venation.

*Texture of bottom surface.*—Slightly coarse due to bulging venation.

*Color.*—Young foliage upper side: Near green 137A RHS. Young foliage under side: Near green 137C RHS. Mature foliage upper side: Near green 137A RHS. Mature foliage under side: Near green 137C RHS.

*Venation.*—Type: Venation color upper side: Near yellow-green 147C RHS. Venation color under side: Near yellow-green 147C RHS.

*Petiole.*—Average Length: Approximately 2-3 cm. Diameter: Approximately 0.15 cm. Color: Near yellow-green 146C RHS.

FLOWER

Natural flowering season: Under moderate climate such as in Israel — From end of Winter to late Fall. (February-November). Under cooler weather conditions will flower from April to September.

Inflorescence type and habit: From each main lateral branch 3-5 inflorescences spikes will emerge.

Flower longevity on plant: 5-7 days.

Quantity of flowers: About 10-15 blooming spikes per plant.

Inflorescence size:

*Diameter.*—Approximately 2.5 cm.

*Height.*—Approximately 12-15 cm.

*Flowers and buds per inflorescence.*—Average 80.

Peduncle:

*Length.*—3 cm.

*Diameter.*—0.2 cm.

*Texture.*—Lightly pubescence with soft, short feather-like hairs, slightly ribbed longwise.

*Color.*—Near yellow green 146B RHS.

*Orientation.*—45 degrees upright from main branch or lateral branch.

*Strength.*—Strong but flexible, not easily breakable.

*Petal arrangement.*—The corolla is sympetalous and typically bilabiate with 2 small, highly fused lobes forming an upper lip and 3 larger highly fused lobes forming a lower lip.

Individual flowers:

*Size.*—Diameter: Approximately 0.5 cm. Length: Approximately 1 cm. Persistence: Non-persistent. Fragrance: Delicate sage — like fragrance.

*Petals.*—Margin: Upper lip — entire. Lower lip — pinnate. Tip shape: Upper lip: 2 fused lobe forming 3 dimensional "V" tip shape. Lower lip: 3 fused lobe forming obtuse tip shape. Length: Upper lip: 0.6 cm. Lower lip: 0.5 cm. Tube: 0.4 cm. Width: Upper lip: 0.25 cm. Lower lip: 0.5 cm. Tube: 0.25 cm. Texture: Upper lip: Smooth, slightly pubescence, matte. Lower lip: Smooth. Tube: Smooth, transparent, slightly ribbed longwise.

*Color.*—Upper Lip: When opening: Inner surface: Near violet purple N94B RHS. Outer surface: Near violet purple N94A RHS. Fully opened: Inner surface: Near violet purple N94C RHS. Outer surface: Near violet purple N94B RHS. Fading: Inner surface: Near violet purple N93A RHS. Outer surface: Near violet purple N93B RHS.

*Color.*—Lower Lip: When opening: Inner surface: Near N89A RHS. Outer surface: Near N89B RHS. Fully opened: Inner surface: Near N89A RHS. Outer surface: Near N89C RHS. Fading: Inner surface: Near violet purple 93A RHS. Outer surface: Near violet purple 93B RHS.

*Color.*—Tube: When opening: Inner surface: Near violet group 85D RHS. Outer surface: Near violet group 84D RHS. Fully opened: Inner surface: Near violet group 85D RHS. Outer surface: Near violet group 84D RHS. Fading: Inner surface: Near violet group 85C RHS. Outer surface: Near violet group 85C RHS.

*Bud*.—Shape: Elliptical. Length: 0.8 cm. Diameter: 0.2 cm. Color: Near Violet group 95A RHS.

*Sepals*.—Shape: 2 Sepals fused to be a tube. Length: Approximately 0.7 cm. Width: Approximately 0.4 cm. Margin: Entire. Texture: Lightly pubescent with soft, short feathers like hairs, slightly ribbed longwise. Color: Near purple group N77 RHS.

REPRODUCTIVE ORGANS

Stamens:

*Number*.—2.

*Filament length*.—Approximately 0.5 cm.

Anthers:

*Shape*.—Ellipsoid.

*Length*.—Approximately 0.01 cm.

*Color*.—Near yellow green group 154C RHS.

*Pollen*.—Color: Near greyed yellow group 161D RHS. Quantity: Moderate.

Pistil:

*Number*.—1.

*Length*.—Approximately 1.4 cm.

*Style*.—Length: Approximately 1.2 cm.

*Stigma*.—Shape: "Y" shape. Color: Near violet group 93A RHS. Ovary color: Near yellow-green group 154B RHS.

OTHER CHARACTERISTICS

Seeds and fruits: 1-2 seeds per flower. Round, minute, approximately 0.1 cm diameter. Dark brown to black, not RHS measurable.

Disease/pest resistance: Neither resistance nor susceptibility to normal diseases and pests of *Salvia* have been observed.

What is claimed is:

1. A new and distinct cultivar of *Salvia* plant named 'DSALRS203' as herein illustrated and described.

* * * * *